US010821805B2

(12) United States Patent
Gallagher

(10) Patent No.: US 10,821,805 B2
(45) Date of Patent: Nov. 3, 2020

(54) OCCUPANT THERMAL STATE DETECTION AND COMFORT ADJUSTMENT SYSTEM AND METHOD

(71) Applicant: Gentherm Incorporated, Northville, MI (US)

(72) Inventor: James Francis Gallagher, Walled Lake, MI (US)

(73) Assignee: Gentherm Incorporated, Northville, MI (US)

( * ) Notice: Subject to any disclaimer, the term of this patent is extended or adjusted under 35 U.S.C. 154(b) by 115 days.

(21) Appl. No.: 16/088,314

(22) PCT Filed: Mar. 31, 2017

(86) PCT No.: PCT/US2017/025294
§ 371 (c)(1),
(2) Date: Sep. 25, 2018

(87) PCT Pub. No.: WO2017/173222
PCT Pub. Date: Oct. 5, 2017

(65) Prior Publication Data
US 2019/0084372 A1    Mar. 21, 2019

Related U.S. Application Data

(60) Provisional application No. 62/316,938, filed on Apr. 1, 2016.

(51) Int. Cl.
*B60H 1/00* (2006.01)
*A61B 5/01* (2006.01)
(Continued)

(52) U.S. Cl.
CPC ....... *B60H 1/00742* (2013.01); *A61B 5/0075* (2013.01); *A61B 5/0077* (2013.01);
(Continued)

(58) Field of Classification Search
None
See application file for complete search history.

(56) References Cited

U.S. PATENT DOCUMENTS 4,024,725 A   5/1977   Uchida et al.
4,920,759 A   5/1990   Tanaka et al.
(Continued)

FOREIGN PATENT DOCUMENTS

DE   102013007080 A1   3/2014
EP      1468851 A1   10/2004
(Continued)

OTHER PUBLICATIONS

International Search Report and Written Opinion for International Application No. PCT/US2017/025294 dated Jun. 30, 2017.
(Continued)

*Primary Examiner* — Paul B Yanchus, III
(74) *Attorney, Agent, or Firm* — Carlson, Gaskey & Olds, P.C.

(57) ABSTRACT

A method for controlling a thermal state of a vehicle occupant, includes obtaining an infrared (IR) image of a face of the occupant using a passive infrared sensor (PIR) sensor. The IR image comprising a spatial array of facial temperatures and receives the image in a controller. A first segment of the array is determined based on a first facial temperature associated with the first segment using the controller. The first segment corresponds to a nose of the occupant. A second segment of the array is determined at least partially surrounding the first segment based on a plurality of second facial temperatures associated with the second segment using the controller. The second segment corresponds to a region of the face surrounding the nose. A difference is determined based on the first facial temperature and at least one of the second facial temperatures using the controller.

(Continued)

The thermal state of the occupant is determined based on the difference.

26 Claims, 7 Drawing Sheets

(51) Int. Cl.
G06K 9/00 (2006.01)
A61B 5/00 (2006.01)
G06K 9/20 (2006.01)
A61B 5/18 (2006.01)
G01J 5/00 (2006.01)
G05B 19/042 (2006.01)

(52) U.S. Cl.
CPC ............... *A61B 5/015* (2013.01); *A61B 5/18* (2013.01); *A61B 5/6893* (2013.01); *G01J 5/0025* (2013.01); *G05B 19/042* (2013.01); *G06K 9/00362* (2013.01); *G06K 9/00845* (2013.01); *G06K 9/2018* (2013.01); *G01J 2005/0081* (2013.01); *G05B 2219/2614* (2013.01)

(56) References Cited

U.S. PATENT DOCUMENTS

| | | | |
|---|---|---|---|
| 2001/0039806 A1 | 11/2001 | Kawai et al. | |
| 2014/0313309 A1 | 10/2014 | Matsuo | |
| 2015/0233598 A1* | 8/2015 | Shikii | F24F 11/79 165/244 |
| 2015/0247647 A1* | 9/2015 | Kusukame | H04N 5/23245 700/276 |

FOREIGN PATENT DOCUMENTS

| | | |
|---|---|---|
| GB | 1232048 A | 5/1971 |
| JP | S5595054 A | 7/1980 |
| JP | S5737642 A | 3/1982 |
| JP | S6027904 A | 2/1985 |
| JP | S6092919 A | 5/1985 |
| JP | S62125243 A | 6/1987 |
| JP | S62299420 A | 12/1987 |
| JP | H01229713 A | 9/1989 |
| JP | H02136321 A | 5/1990 |

OTHER PUBLICATIONS

Taniguchi, Yousuke, et al., "Study on car air conditioning system controlled by car occupants' skin temperatures—part 1: research on a method of quantitative evaluation of car occupants' thermal sensations by skin temperatures," SAE Technical Paper Series, Feb. 24-28, 1992.

Tanaka, Hisashi, et al., "Study on car air conditioning system controlled by car occupants' skin temperatures—part 2: development of a new air conditioning system," SAE Technical Paper Series, Feb. 24-28, 1992.

International Preliminary Report on Patentability for PCT Application No. PCT/US2017/025294 dated Oct. 11, 2018.

* cited by examiner

OCCUPANT THERMAL STATE DETECTION AND COMFORT ADJUSTMENT SYSTEM AND METHOD

CROSS-REFERENCE TO RELATED APPLICATIONS

This application claims priority to U.S. Provisional Application No. 62/316,938, which was filed on Apr. 1, 2016 and is incorporated herein by reference.

BACKGROUND

This disclosure relates to system of detecting occupant thermal state and comfort and a method of adjusting same.

A typical automotive thermal comfort systems relies upon an occupant input for controlling such thermal conditioning system components as the central HVAC and climate controlled seats. In automatic HVAC systems the occupant sets a desired cabin temperature. In climate controlled seat systems, the occupant initially sets a desired level of heating or cooling (e.g. low, medium, high settings) to achieve thermal comfort, and then manually adjusts the setting to maintain comfort or avoid discomfort that may be caused by overheating or overcooling.

An imaging system including an infrared (IR) sensor can be used to detect the presence of a human within a surrounding image. IR sensors are used for a variety of applications, including motion detection systems for lighting and security as well as deployment of airbags in automobiles.

Conventional thermal comfort systems can be improved by detecting the occupant's thermal state and making adjustments without occupant input that move the occupant towards a more comfortable state and avoid overshooting to an uncomfortable state that requires the occupant to intervene with an input adjustment. There has been some effort to use IR sensors within a vehicle cabin to thermally image an occupant's face and then control a vehicle thermal conditioning system based upon detected thermal image. There has not been much development of this technology, however, to ensure that the detected occupant thermal state can be closely correlated with the occupant's actual thermal comfort.

SUMMARY

In one exemplary embodiment, a method for controlling a thermal state of a vehicle occupant, includes obtaining an infrared (IR) image of a face of the occupant using a passive infrared sensor (PIR) sensor. The IR image comprising a spatial array of facial temperatures and receives the image in a controller. A first segment of the array is determined based on a first facial temperature associated with the first segment using the controller. The first segment corresponds to a nose of the occupant. A second segment of the array is determined at least partially surrounding the first segment based on a plurality of second facial temperatures associated with the second segment using the controller. The second segment corresponds to a region of the face surrounding the nose. A difference is determined based on the first facial temperature and at least one of the second facial temperatures using the controller. The thermal state of the occupant is determined based on the difference.

In a further embodiment of the above, the first segment has a polygonal shape with at least N sides and the second segment surrounds the first segment on at least N-1 sides. N is an integer greater than or equal to three.

In a further embodiment of any of the above, the second segment is in a shape of an inverted U.

In a further embodiment of any of the above, the second segment includes a portion of the forehead and a portion of each check.

In a further embodiment of any of the above, the first segment includes at least a portion of a tip of the nose.

In a further embodiment of any of the above, the tip is provided by at least five pixels.

In a further embodiment of any of the above, the tip is provided by at least twelve pixels.

In a further embodiment of any of the above, the method includes obtaining a plurality of first facial temperatures within the first segment corresponding to the nose at successive T times in a period using the PR sensor. T is an integer greater than or equal to 2. A plurality of second facial temperatures corresponding to the region of the face surrounding the nose at the T times using the PIR sensor is obtained. A plurality of differences at the T times using the controller is determined. A trend in the differences is determined. A thermal comfort of the occupant based on the trend in the differences is also determined.

In a further embodiment of any of the above, a temperature comparison value from memory is received. It is determined when the occupant is experiencing discomfort when the trend is increasing and the latest difference is greater than the temperature comparison value using the controller.

In a further embodiment of any of the above, the temperature comparison value corresponds to at least one of occupant thermal sensation and occupant thermal comfort.

In a further embodiment of any of the above, at least one of occupant thermal sensation and occupant thermal comfort is based respectively on the Berkeley Sensation and Comfort Scale.

In a further embodiment of any of the above, a temperature comparison value from memory of the controller is retrieved. The temperature comparison value is associated with one of a vasoconstricted state and a vasodilated state. The difference and the temperature comparison value is compared the using the controller.

In a further embodiment of any of the above, a thermal conditioning device in the vehicle that heats or cools an occupant of the vehicle at a variable heat rate is provided. The variable heat rate based on the thermal state of the occupant is adjusted.

In a further embodiment of any of the above, the method includes the step of commanding the thermal conditioning device based upon the difference. The adjusting step is performed in response to the commanding step.

In a further embodiment of any of the above, the first segment is spaced from the second segment.

In a further embodiment of any of the above, the nose is discrete from the second segment.

In another exemplary embodiment, a thermal conditioning system includes a thermal conditioning device. An infrared sensor is configured to detect an occupant thermal facial image. A controller is in communication with the thermal conditioning device and the infrared sensor. The controller is configured to isolate a nose thermal state from the occupant thermal facial image and infer a current occupant thermal condition based upon the nose thermal state. The controller is configured to command the thermal conditioning device based upon the current occupant thermal condition relative to a temperature comparison value to achieve a desired occupant thermal condition.

In a further embodiment of any of the above, the thermal conditioning device is at least one of an HVAC thermal conditioning system, a steering wheel, a seat, a door panel, an armrest, a window defogger, a dash panel and a roof panel.

In a further embodiment of any of the above, a nose is isolated with reference to a portion of the forehead and a portion of each check.

In a further embodiment of any of the above, the nose thermal state is associated with a tip of the nose.

In a further embodiment of any of the above, the current occupant thermal condition corresponds to at least one of an occupant thermal sensation and an occupant thermal comfort.

In a further embodiment of any of the above, at least one of occupant thermal sensation and occupant thermal comfort is based respectively on the Berkeley Sensation and Comfort Scale.

In a further embodiment of any of the above, the desired occupant thermal condition corresponds to a temperature comparison value for the nose thermal state. The controller is configured to command the thermal conditioning device to urge the nose thermal state to the temperature comparison value.

In another exemplary embodiment, a method of controlling a thermal state of a vehicle occupant includes detecting an occupant thermal facial image and isolating a nose thermal state from the occupant thermal facial image. A current occupant thermal condition is inferred based upon the nose thermal state. A thermal conditioning device is commanded based upon the current occupant thermal condition relative to achieve a desired occupant thermal condition.

In a further embodiment of any of the above, the detecting step includes scanning a vehicle cabin with an infrared sensor to acquire a spatial array of facial temperatures from the occupant thermal facial image.

In a further embodiment of any of the above, the isolating step includes detecting a first segment corresponding to a nose of an occupant. A second segment discrete from the first segment and at least partially surrounding the nose is detected.

In a further embodiment of any of the above, the inferring step includes comparing the nose thermal state to a temperature comparison value indicative of the desired occupant thermal condition.

In a further embodiment of any of the above, the temperature comparison value is a stored data set specific to an occupant.

In a further embodiment of any of the above, the inferring step is performed at intervals over a period of time.

In a further embodiment of any of the above, the thermal conditioning device is at least one of an HVAC thermal conditioning system, a steering wheel, a seat, a door panel, an armrest, a window defogger, a dash panel and a roof panel.

BRIEF DESCRIPTION OF THE DRAWINGS

The disclosure can be further understood by reference to the following detailed description when considered in connection with the accompanying drawings wherein.

The embodiments, examples and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

DETAILED DESCRIPTION

It is difficult to objectively quantify a person's thermal state, e.g., sensations and comfort, (collectively referred to as "occupant thermal condition") such that a thermal conditioning system can be automatically controlled to achieve a desired thermal sensation and comfort for that person. As one example, an occupant thermal condition or state can be a condition of sensing a hot or cold temperature, or changes in temperature. As another example, an occupant thermal condition or state can be a condition of feeling comfortable or uncomfortable, a level of comfort, or a change in a level of comfort. One widely recognized approach that attempts to objectively quantify a person's thermal condition is referred to as the Berkeley Sensation and Comfort Scale ("Berkeley scale"), described in, for example, Arens E. A., Zhang H. & Huizenga C. (2006) Partial- and whole-body thermal sensation and comfort, Part I: Uniform environmental conditions. *Journal of Thermal Biology*, 31, 53-59. It should be understood that other approaches can be used to quantify an occupant's thermal condition.

Using the Berkeley scale, thermal sensation is quantified from +4 to −4 by a person. A more positive number corresponds to an increasing degree of perceived heat, and a more negative number corresponds to an increasing degree of perceived cold. High positive or negative numbers are indicative of painfully hot or painfully cold conditions respectively. A zero indicates the person is neutral as to any thermal sensation. Thermal comfort on the Berkeley scale is quantified from +4 to −4 by a person, where a +4 indicates a person is "very comfortable," and a −4 indicates a person is "very uncomfortable."

Such a scale can be used to provide stored reference values, along with cabin temperature and vehicle exterior temperature, for example, by the system to both identify the current occupant thermal condition and control the system to achieve a desired occupant thermal condition. For example, the system may identify an occupant with a thermal sensation of +2 and a thermal comfort of −3, which indicates the occupant feels hot and very uncomfortable. The system will then control one or more thermal conditioning devices to achieve, for example, a thermal sensation of 0 and a thermal comfort of +1 in as short of a time as possible without overshooting the desired thermal sensation. The cabin temperature and vehicle outside temperature may be used to determine how to best achieve the desired occupant thermal condition.

Figure 2:
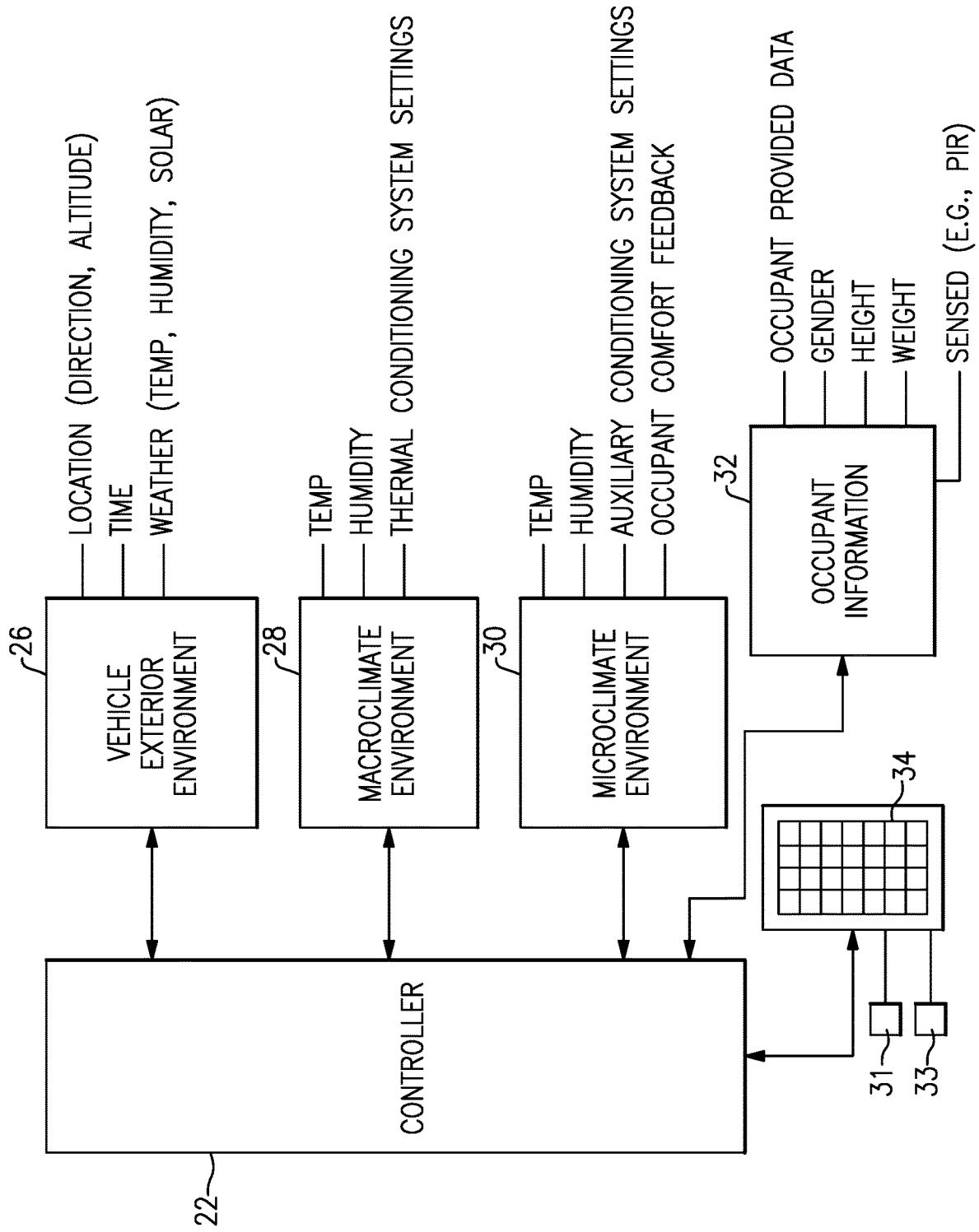
FIG. 2 is a schematic view of a controller of the microclimate system and example inputs provided to the controller for the system of FIG. 1.
Figure 3:
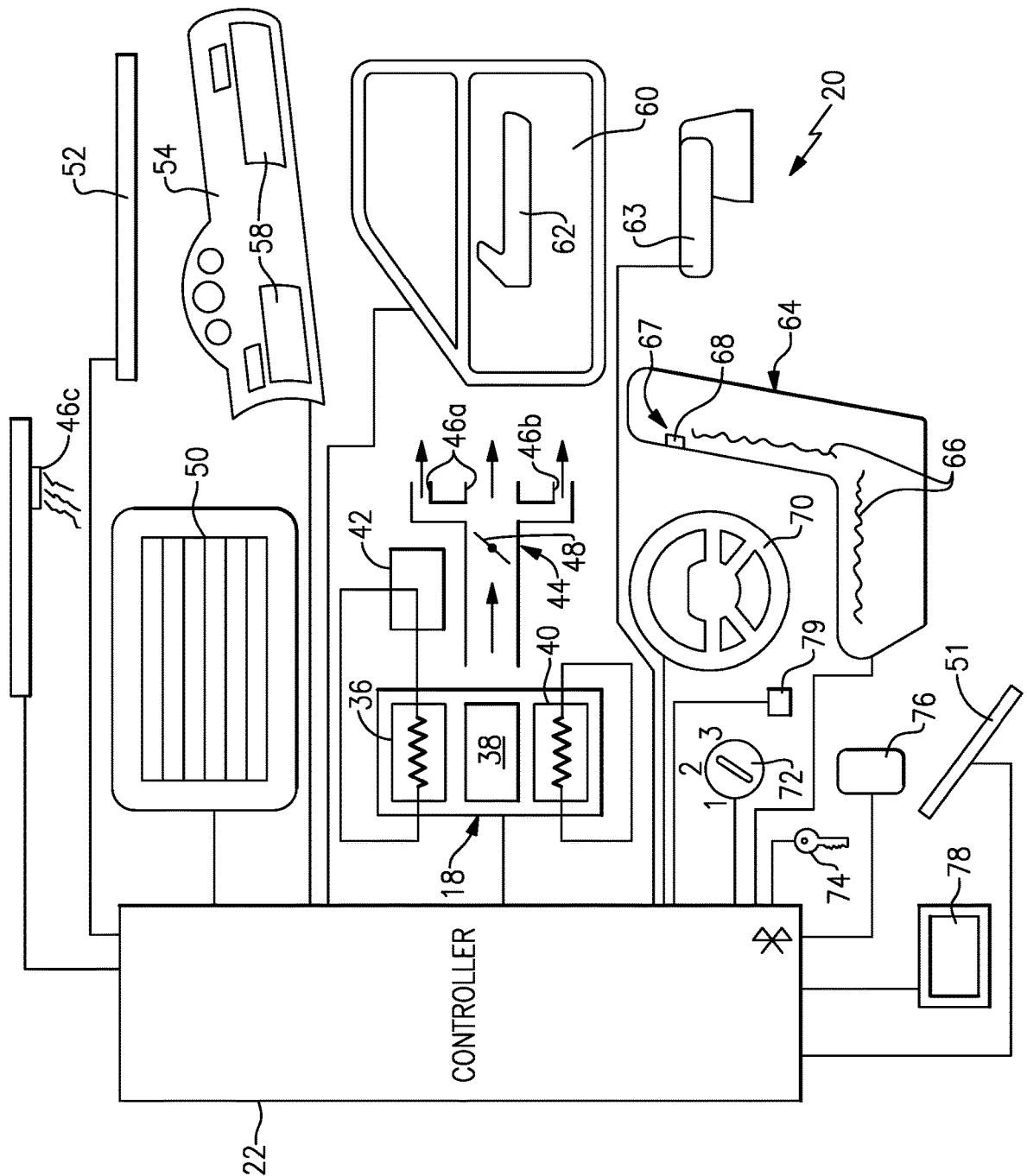
FIG. 3 is a schematic view of the controller in communication with macroclimate devices and microclimate devices for the system of FIG. 1.

An example vehicle thermal conditioning system is shown in FIGS. 2-3. One example vehicle thermal conditioning system is disclosed in International Application No. PCT/US2015/058328, entitled "VEHICLE MICROCLIMATE SYSTEM WITH TARGETED VASODILATION OF EXTREMITIES FOR IMPROVED OVERALL THERMAL COMFORT AND METHOD OF CONTROLLING SAME," filed on Oct. 30, 2015, which is incorporated by reference in its entirety.

Each occupant typically has a unique occupant personal comfort. That is, a particular occupant detects a level of thermal energy differently than another occupant. As a result, the exact same thermal environment within a vehicle may be perceived as comfortable by one occupant, but as uncomfortable by another occupant. To this end, this disclosure relates to providing an integrated approach to human thermal management by controlling and coordinating both macroclimate devices (e.g., central HVAC system) and microclimate devices (e.g., climate controlled seats (e.g., U.S. Pat. Nos. 5,524,439 and 6,857,697), head rest/neck conditioner (e.g., U.S. Provisional App. No. 62/039,125), climate controlled headliner (e.g., U.S. Provisional App. No. 61/900,334), steering wheel (e.g., U.S. Pat. No. 6,727,467 and U.S. Pub. No. 2014/0090513), heated gear shifter (e.g., U.S. Pub. No. 2013/0061603, etc.) to achieve a personalized microclimate system. The microclimate system provides desired occupant personal comfort in a more automated manner with little or no input from the occupant. It should be understood that microclimate devices alone (i.e. without a macroclimate device) can provide both a macroclimate and a personalized microclimate within the macroclimate. The referenced patents, publications and applications are incorporated herein by reference in their entirety.

The present disclosure provides a system that determines a thermal state of the occupant by measuring facial temperatures and distinguishing nose temperatures or condition from temperatures of the surrounding cheeks and forehead. Then, by comparing the nose temperatures and the surrounding temperatures, the system can detect the thermal state of the occupant. More particularly, the system can detect the occupant's thermoregulatory state, which can range from a vasoconstricted state to a vasodilated state. The disclosed system can also determine a trend in the thermal state to determine whether the occupant is moving from an uncomfortable state to a comfortable state and vice-versa.

The disclosed system uses a passive infrared (PR) sensor to obtain an infrared (IR) image of a face of the occupant. A controller determines segments of the thermal image corresponding to the nose of the occupant and surrounding cheeks and forehead. The system determines a difference in the nose temperatures and the surrounding cheeks and/or forehead, and determines the thermal state of the occupant based on the difference. The system monitors a trend in the thermal state, and adjusts a rate of heating or cooling of the occupant based on the occupant's thermal state and trend in the state.

Figure 1:
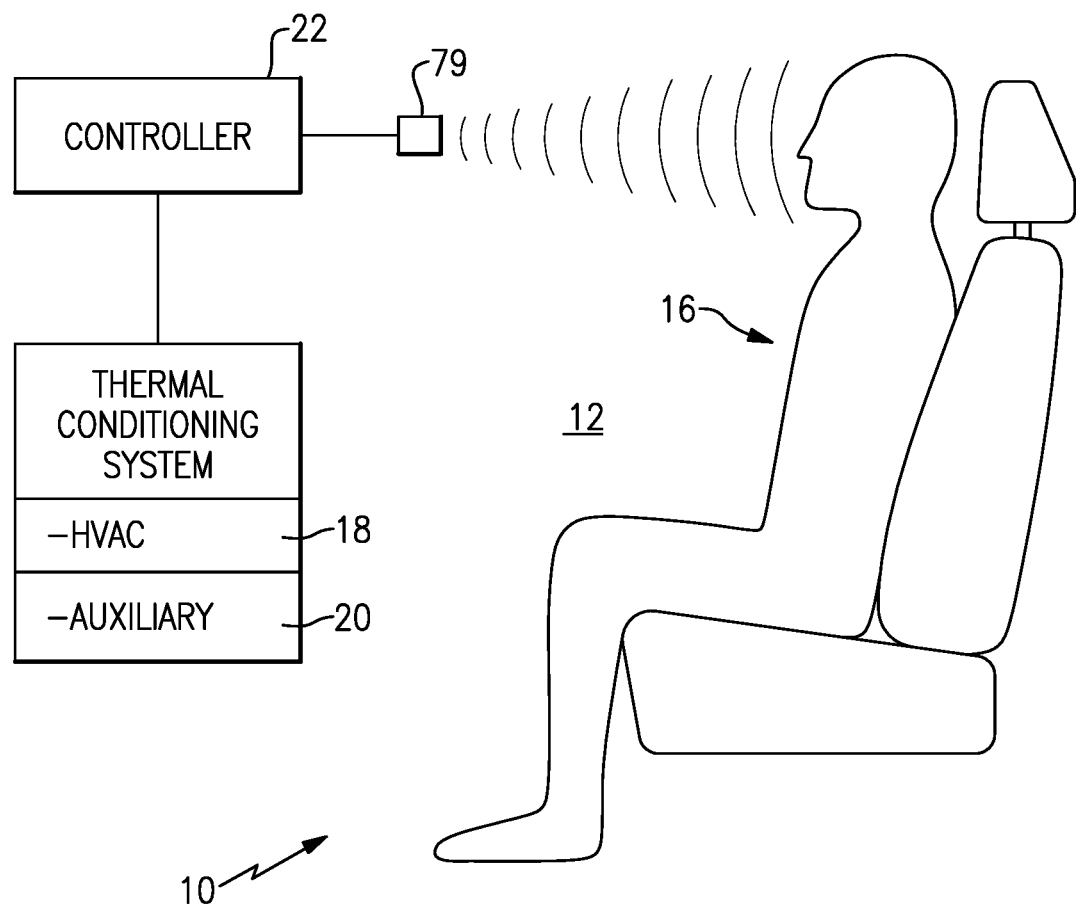
FIG. 1 schematically depicts an occupant in a vehicle seat and a thermal conditioning system that includes an infrared sensor used to determine occupant thermal condition.

In one example, the vehicle 10 includes an HVAC thermal conditioning system 18 and an auxiliary thermal conditioning system 20 (with microclimate devices), which are in communication with a controller 22, as shown in FIG. 1. Various inputs, for example, a PIR sensor 79, 24 may communicate with the controller 22 to affect and control operation of the HVAC thermal conditioning system 18 and/or the auxiliary thermal conditioning system 20 to regulate an interior space 12 for an occupant 16.

In one example microclimate system, the controller 22 receives various inputs via sensors and/or devices within the microclimate system, for example, from a vehicle exterior environment 26 shown in FIG. 2. The vehicle exterior environment 26 may include parameters such as vehicle location, vehicle direction and altitude, time of day and date, and weather related parameters (outdoor temperature, outdoor humidity, and solar load on the vehicle).

A macroclimate environment 28 also communicates parameters to the controller 22. The macroclimate environment parameters may include interior temperature and/or humidity at one or more locations, and current HVAC system settings.

A microclimate environment 30 communicates parameters to the controller 22. The microclimate environment parameters may include temperature and/or humidity at one or more microclimate devices, auxiliary conditioning system settings, and occupant comfort feedback. Occupant comfort feedback may be provided when the occupant provides an input to control one of the microclimate devices, such as by changing the position of a switch.

Occupant information 32 is provided to the controller 22 for customizing and accounting for thermoreceptive differences between various occupants. It has been shown, for example, that women and men, generally speaking, react to heat and cold differently, with women reacting more severely and more quickly to cold and men reacting more quickly to heat. Additional factors are, for example, the occupant's body composition, amount of hair, and clothing as well as personal preferences. Additionally, the occupant information 32 can provide information for determining a thermal mass, heat capacity, and internal energy production rate. Occupant information 32 includes such information as gender, height, weight, and other occupant-provided data to provide a user profile. Then, for example, an initial default data set, or microclimate profile, could be defined during the customer vehicle purchase process, prior to any data being collected. Then based on the default microclimate profile the system can begin the process of intuitively collecting data and then adjusting to individual's needs/wants based on the actual inputs by and use from the user over time. This initial microclimate profile could be based on any number of factors, including quantitative factors such as initial purchase location, driver characteristics (sex, height, weight, etc.), as well as qualitative factors, such as a survey where the respondent answers questions about their normal state of thermal comfort/stress. This information, which may create a custom Berkeley-type reference scale for a given occupant, can be stored on a key fob or mobile device that is communicated to the controller 22. The user profile and learned microclimate profile can "move" with the occupant via the vehicle data link, the cloud, wireless transmission and/or smartphone, for example.

Sensed occupant information may also be provided (see, e.g., sensor 79 in FIG. 3), for example, by detecting occupant temperature, as explained in more detail below in connection with FIGS. 6A-9. These sensed occupant personal comfort inputs are provided to the controller 22 for determining a perceived occupant personal comfort. The inputs can include one or more measured physiological parameters such as skin or other body temperatures such as a body core temperature.

Multiple parameters from the vehicle exterior environment 26, the macroclimate environment 28, the microclimate environment 30, and the occupant information 32 may be stored in memory, such as one or more look-up tables 34. The memory may store information relating to one or more user profiles 31 and microclimate profiles 33 for various use scenarios corresponding to a particular user. The controller 22 may learn from adjustments to the microclimate system made by the occupant and update the microclimate profile 33 in the look-up tables 34 so that the occupant personal comfort may be anticipated and the microclimate system adjusted automatically. Interpolation of look-up table values or another suitable method can be used to determine settings between pre-existing set-points. In one example, the controller may store a measured difference between a temperature of the occupant's nose and a temperature of the occupant's face surrounding the nose at the time of or just preceding the time when the occupant adjusted the thermal conditioning provided by the microclimate system.

Referring in FIG. 3, an example HVAC thermal conditioning system 18 is in communication with the controller 22. The HVAC thermal conditioning system 18 includes a heat exchanger 36 in fluid communication with a heating loop connected to an engine 42. The engine 42 may include an internal combustion engine, an electric motor system, and/or a fuel cell. The engine 42 provides a heat source for the HVAC thermal conditioning system 18. An evaporator 40 is arranged in a cooling loop, which may include refrigerant and conventional air conditioning components typically found in a vehicle. It should be understood that a conventional HVAC system can instead be provided by one or more electrically operated microcompressors, if desired. A ventilation system 38, which provides fresh air to the HVAC system, may also be provided. The HVAC thermal conditioning system 18 typically includes ducting 44 providing multiple vents 46a, 46b, 46c. In one example, the vent 46b is directed to a foot well near the occupant's feet, and the vent 46c is provided in a headliner and directed to the occupant's face. One or more valves 48 selectively control airflow from the HVAC system to the vents 46. These HVAC system components provide the macroclimate environment, although the vents may be controlled in a selective manner to provide the microclimate environment.

The auxiliary thermal conditioning system 20 includes multiple microclimate devices, such as a window defroster/defogger 50, a heated floor mat 51, a roof panel 52, one or more panels 58 in an instrument panel 54, a door panel 60, a door arm rest 62, a center console armrest 63, a seat 64 having thermal element 66 and a neck conditioning device 67 having a neck vent 68 (or other neck conditioning device), and/or a steering wheel 70. These microclimate devices are intended to increase occupant comfort beyond what an HVAC system is capable by providing heating and/or cooling in close proximity to an occupant and thereby a more personalized microclimate environment within the surrounding interior environment. Heating and cooling can be provided by, for example, one or more heating elements, fans, thermoelectric devices, heat pumps, and/or microcompressors.

The inputs 24 are used to adjust the macroclimate environment and the microclimate environment through the controller 22 to achieve a desired occupant personal comfort. Inputs 24 include sensor signals and other inputs indicative of various parameters of the vehicle exterior environment 26, the macroclimate environment 28, and the microclimate environment 30. Inputs 24 further include one or more switches 72, a key fob 74 containing occupant information, a mobile device 76 containing occupant information and/or a display 78. The display 78 may visually display outputs or operating modes of the HVAC thermal conditioning system 18 and/or the auxiliary thermal conditioning system 20. The display 74 may also provide a means of input via a touchscreen, for example. The sensor 79, for example, a passive infrared sensor (PIR), may provide real-time, sensed occupant information, such as temperature via a detected infrared (IR) image, moisture, humidity or other information.

Figure 4A:
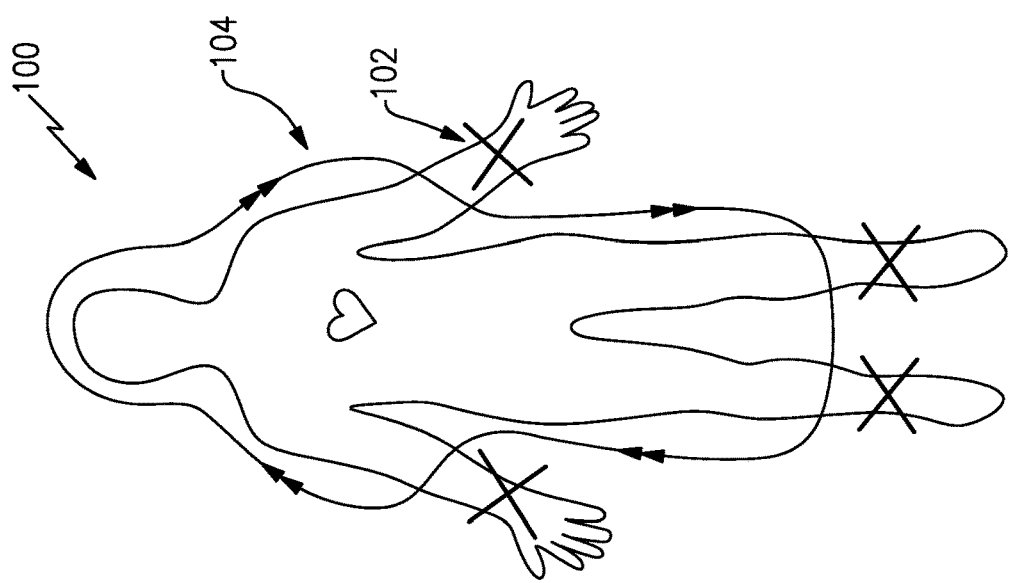
FIG. 4A is a schematic view of blood flow through an occupant's body with its arteriovenous anastomoses (AVAs) vasoconstricted at the extremities.

Temperatures are not uniform throughout the body. Local tissue temperatures are determined primarily by metabolic activity, blood flow, and blood temperature. The body can be compartmentalized based on metabolic activity. For example, referring to FIG. 4A, when the occupant 100 is exposed to a cold environment, the body's thermal management system closes (vasoconstricts) its arteriovenous anastomoses (AVAs) 102 at the extremities (e.g., hands and feet) to maintain the core body temperature. Since the temperature of an occupant's hands and feet significantly impacts the sense of overall thermal comfort, a cold environment exacerbates the occupant's feeling of thermal discomfort because the occupant's extremities are receiving a reduced blood flow 104 from the core body due to the constricted AVAs.

Hands, feet and parts of the face can have such a significant impact on perceived thermal comfort due the type of skin present. The presence or absence of hair follicles defines two types of skin: hairy (or non-glabrous), or non-hairy (glabrous). Nutrient blood flow to these two skin types is similar, but blood flow for heat dissipation is confined only to the glabrous skin regions. Underlying glabrous skin areas—the palms of hands, soles of the feet, and parts of the face and ears—are natural heat exchange portals with unique vascular network structures beneath the surface of the skin.

Figure 4B:
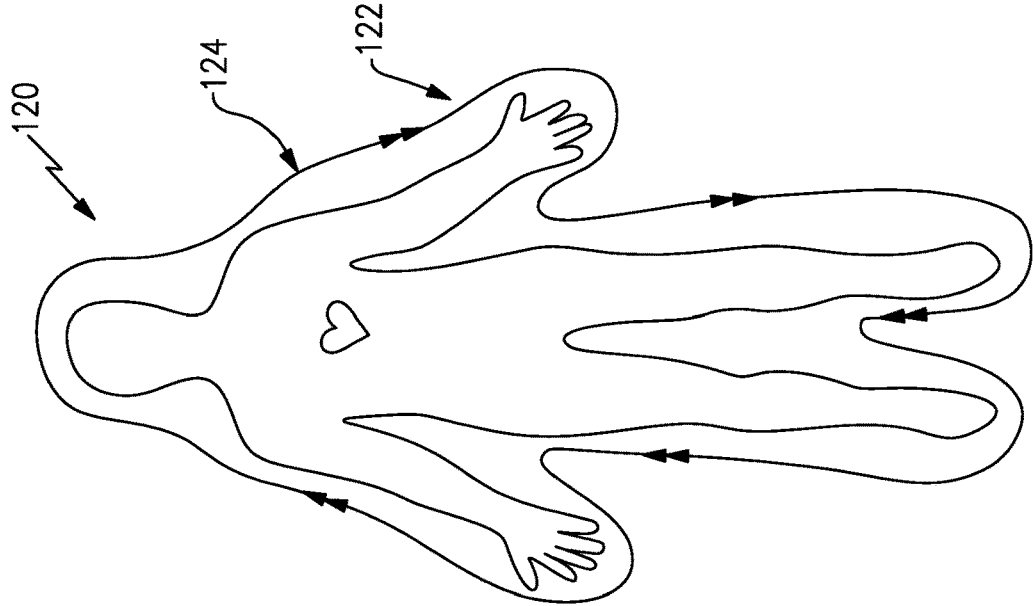
FIG. 4B is a schematic view of blood flow through the occupant's body with the AVAs vasodilated.
Figure 5:
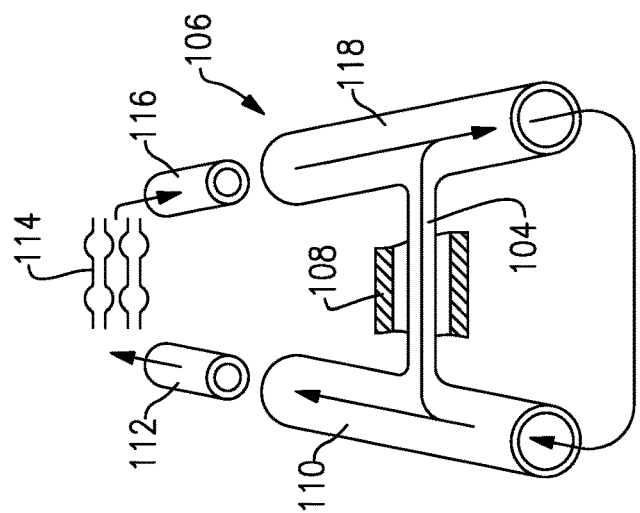
FIG. 5 is a schematic view of a blood circulatory system at an extremity of the occupant's body.

These specialized circulatory networks 106 of glabrous skin are shown schematically in FIG. 5. Blood circulates out from the heart through arteries 110 to arterioles 112. Papillary capillaries 114 within the glabrous regions are located above the AVAs 104, which interconnect the artery 110 to the vein 118. The capillaries 114 enable heat exchange due to their low mass and high surface area. The AVAs 104 are gated by smooth muscle 108. When the AVAs are closed (FIG. 5A), capillaries limit blood flow as they connect the arterioles 112 and venules 116, the small dimension vessels in the microcirculatory system which act as the connectors between arteries 110 and veins 118 respectively to capillaries 114, for carrying nutrients to and removing waste from the surrounding tissues. However, when the AVAs are open (FIG. 4B), a lower path of resistance is created directly between the arteries and veins allowing a significantly higher blood flow rate within this region, enabling increased blood flow 124 in the extremities 122 of the occupant 120.

When the pathway is opened, the AVAs enable a significant increase in blood flow beneath the skin in glabrous regions, as shown in FIG. 4B. Dilation and contraction of the AVAs are controlled by the body's thermoregulatory system. When the body perceives conditions which would cause its temperature to rise above normal, the AVAs dilate to increase blood flow near the skin surface, thereby increasing heat loss to the environment. When the body perceives conditions leading to a decrease in core temperature, the AVAs constrict, decreasing blood flow, allowing the body to conserve more of its metabolic heat. A vasoconstricted individual has cooler palms than a vasodilated individual, but other areas of their bodies have similar temperatures. Additional access points for glabrous thermal transfer can be seen on the face of a vasoconstricted individual where the temperature of the nose is measuring a cooler temperature than surrounding areas, yet a comparable temperature to this individual's hand.

The AVAs are direct shunts between arteries and veins that bypass capillaries, and provide a low-resistance pathway for the movement of blood through the glabrous skin regions. The receiving venous structures (retia venosa) are arranged in a plexus or large network of vessels that has a large surface-to-volume ratio and can contain a large volume of blood. Thus, the venous plexus acts as a radiator. Vasodilation defines the condition in which the AVAs are open and blood is flowing freely through the venous plexuses; vasoconstriction defines the condition in which the AVAs are closed and blood is not flowing through the venous plexuses.

The human body employs a thermal management system in which AVAs are constricted to maintain the body's heat within its core. When a warm stimulus is applied to the back of the neck (or specifically the cervical spine), the body's core thermal management system interprets this thermal input as the body having excessive heat that it needs to dissipate via its natural heat exchangers—the hands, feet, and parts of the face—and will switch out of heat conservation mode thereby opening the AVAs. When the AVAs are open, there is a very high blood flow, and therefore heat transport, into the low resistance venous radiators; when the AVAs are closed, a greatly reduced blood flow goes through the high-resistance capillaries of the skin. In the normothermic individual, a person whose thermoregulation is within the normal range, proportional control of the AVAs balances internal heat production and heat loss.

In particular, in a cold environment, the human body employs a thermal management system in which AVAs are constricted to maintain the body's heat within its core. When a warm stimulus is applied to the back of the neck (or specifically the cervical spine), the body's core thermal management system thinks it has excessive heat that it needs to dissipate via its natural heat exchangers—the hands, feet, and parts of the face (nose or forehead)—and will switch out of heat conservation mode. The controller 22 determines that the occupant perceives thermal discomfort (too hot or too cold) as a function of temperature, conditioned surface area and exposure time, for example using the infrared sensor 79. The perceived thermal discomfort can be used to infer the state of the AVAs (vasoconstricted or vasodilated).

The thermal conditioning system can be accurately controlled by "reading" the thermal condition (e.g., sensation and comfort) of the occupant, with reference to the state of the AVAs if desired, without the occupant providing control inputs to the system.

Figure 6A:
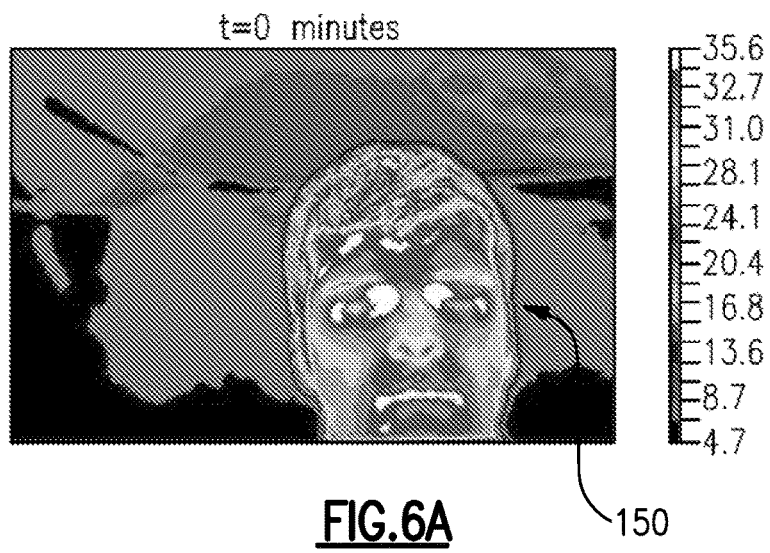
FIG. 6A-6C are thermal images for an example occupant face within a vehicle at time=0 minutes, time=4 minutes and time=8 minutes.
Figure 6B:
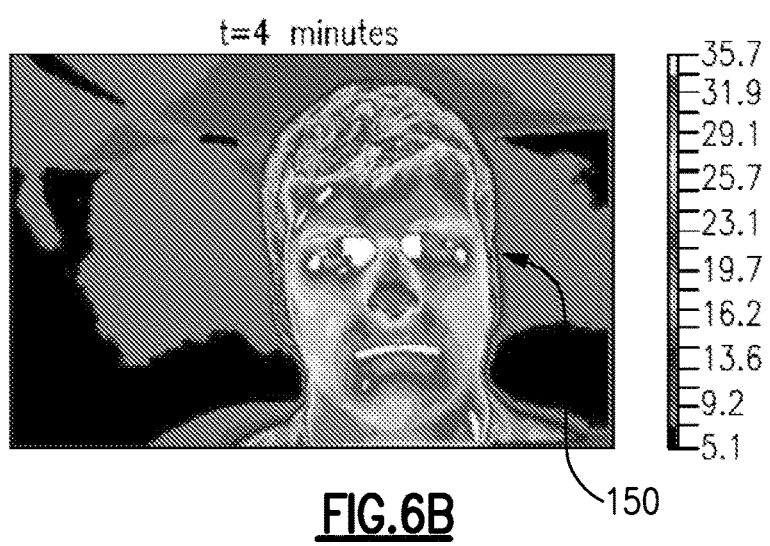
Figure 6C:
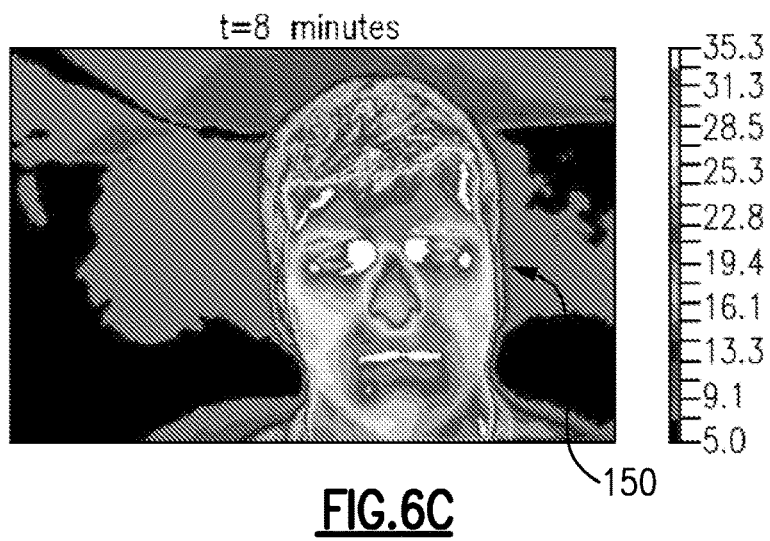
Figure 8A:
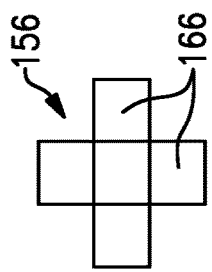
FIGS. 8A-8B illustrate a first segment of a spatial array of facial temperatures corresponding to a tip of a nose.
Figure 8B:
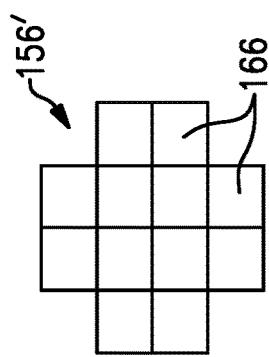
Figure 7:
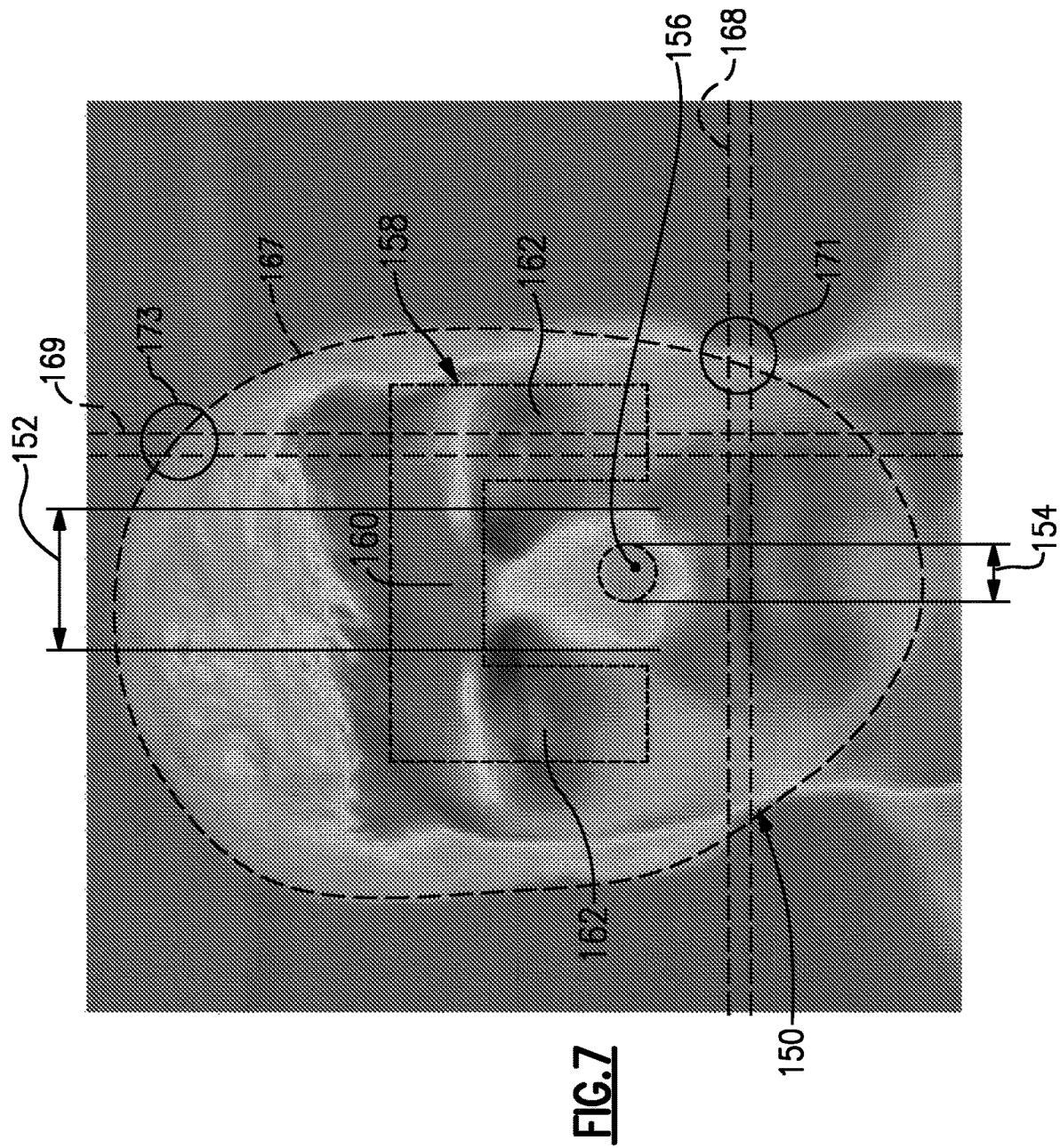
FIG. 7 depicts a thermal image of an occupant face illustrating recognition of a nose relative to a segment surrounding the nose.

The infrared sensor 79 is configured to detect an occupant thermal facial image 150, shown in FIGS. 6A-6C, which indicates the thermal facial image at different intervals (e.g., 0 minutes, 4 minutes and 8 minutes) during a period of time. An IR image of a face of the occupant is obtained using the sensor 79, where the IR image comprises a spatial array of facial temperatures. The temperature scale in the Figures is provided in Celsius and is indicative of the detected surface temperature.

The controller 22 is in communication with the thermal conditioning device and the infrared sensor 79 to receive the thermal image of facial temperatures. The controller 22 is configured to isolate a nose thermal state from the occupant thermal facial image and infer a current occupant thermal condition based upon the nose thermal state. In one example, a first segment 152 of the array is determined based on a first facial temperature associated with the first segment using the controller. The first segment 152 corresponding to a nose 154 of the occupant (FIG. 7), which is greatly impacted by the surrounding temperature and exposure time. In one example, the first segment has a polygonal shape with at least N sides, provided by one or more pixels from the spatial array. The first segment 152 includes at least a portion of a tip 156 of the nose 154. In one example, the tip 156 is provided by at least five pixels 166 (FIG. 8A), and in another example, the tip 156' is provided by at least twelve pixels 166.

A second segment 158 of the array is determined and at least partially surrounding the first segment 152 based on a plurality of second facial temperatures associated with the second segment 158 using the controller. As can be appreciated from FIGS. 6A-7, the temperature of the nose can be significantly different than the surrounding facial region. In one example, the second segment 158 surrounds the first segment on at least N-1 sides, where N is an integer greater than or equal to three. In the example, the first segment 152 is spaced from the second segment 158 so as to avoid a situation where the nose temperature could be an average of an adjoin temperature that might be quite different than the nose. In this manner, the nose temperature is maintained as discrete from the second segment 158. The second segment 158 is in a shape of an inverted U, for example, and includes a portion of the forehead 160 and a portion of each check 162. This approach leads to accurate isolation of the nose, although other approaches may be used.

In various embodiments, an area of interest 167 corresponding to the occupant's head can be determined from a field of view corresponding to the entire IR image by comparing temperatures of successive pixels along image segments 168, 169 and discerning abrupt changes in temperature 171, 173 along the segments 168, 169. The first segment 152 can be determined from the area of interest or head area, by processing image segments at or near the center of the area of interest where the nose is likely to be located. The area of interest can be distinguished from a background area by comparing the temperatures along the image segments 168, 169 to the cabin and exterior temperatures, and a normal temperature of the occupant.

Returning to FIGS. 6A-6C, a plurality of first facial temperatures within the first segment 152 is obtained that corresponds to the nose at successive T times in a period using the sensor 79, where T is an integer greater than or equal to 2. A plurality of second facial temperatures corresponding to the region of the face surrounding the nose is also obtained at the T times using the sensor 79. A plurality of differences at the T times is determined using the controller 22 to determine a trend in the differences. A thermal comfort of the occupant based on the trend in the differences is determined, which reveals, for example, how rapidly the occupant is becoming cold or warm. The size of the difference is also indicative of the occupant's thermal condition.

A temperature comparison value from memory is received by the controller 22 that provides reference data of what a comfortable or uncomfortable occupant might look like. It can then be determined if the occupant is experiencing discomfort when the trend is increasing and the latest difference is greater than the temperature comparison value using the controller 22. The temperature comparison value corresponds to at least one of occupant thermal sensation and occupant thermal comfort based upon, for example, the Berkeley Sensation and Comfort Scale. The temperature comparison value may be associated with one of a vasoconstricted state and a vasodilated state, which can be used to more effectively control the thermal conditioning system. The difference and the temperature comparison value are compared, the thermal state of the occupant is determined, and the thermal conditioning device is commanded based upon the difference to achieve a desired occupant thermal condition.

Feedback also may be provided by the occupant by providing additional inputs via switches or other input devices, which indicates that the occupant is not yet comfortable, or by actively sensing the comfort of the occupant.

The controller 22 learns from the settings typically used by the occupant for a given set of conditions. The controller 22 also learns from adjustments to the settings during periods of automatic control when the microclimate system is operating according to an occupant's microclimate profile 33 associated with their user profile 31. For example, the seat neck warmer could be triggered in order to vasodilate blood flow to the hands while coordinating the conditioning of the steering wheel to achieve maximum thermal comfort perception on the part of the driver, as explained above. When the vehicle learns what a particular occupant likes, based on their not adjusting the thermal management system during operation, those same conditions can be replicated the next time that they occur.

The HVAC system is largely used to change the equilibrium point of the cabin environment, while the auxiliary thermal comfort system 20 manages the perception of comfort by the occupant. This may enable a reduction in HVAC system size since the thermal comfort of the occupant can be more directly manipulated by more targeted, localized devices. Furthermore, the effort of the two systems can be coordinated to limit the need for the occupant to intervene to change the control settings during operation.

The microclimate system and its controller can be designed using one or more methodologies. For example, an "open loop" methodology may be used wherein a particular model is implemented in a computing platform, which may or may not be in the vehicle. This model is then utilized to determine how occupant thermal comfort should be manipulated. The model may be populated using data from off-line testing and validation, and then the appropriate control effects would be created based on sensor input (e.g., humidity, external temperature, etc.).

A "closed loop" methodology may be used wherein a system (e.g., with an infrared camera being a part of the safety system as well as a humidity sensor) ascertains the condition of an occupant, such as a driver, and adjusts thermal conditions based on this information. For example, image processing techniques could determine that the driver is wearing a hat or that the driver is overheated due to exercise based on infrared (IR) imaging.

A "learning" methodology may be used where the closed loop or open loop methodology is modified over time based on the choices made by a particular occupant or set of occupants to adjust the microclimate profile 33. For example, a vehicle may record the outside temperature, inside temperature, and humidity on the look-up tables 34, and remember the thermal control settings chosen by the driver in these conditions, which could then be replicated (or interpolated) then next time that similar conditions are encountered. The longer that the driver uses the vehicle, the more information that is available, and the more "customized" the microclimate profile for the microclimate system will be to that particular individual. Furthermore, an excellent metric for the suitability of any set of parameters given a particular set of conditions would likely be how long the system is left in a particular state, that is, without an occupant adjusting any thermal settings. Occupant personal comfort inputs may also be evaluated (32 in FIG. 2), for example, by using an infrared camera (e.g., sensor 79 in FIG. 3) to detect a body temperature or other condition of the occupant.

Figure 9:
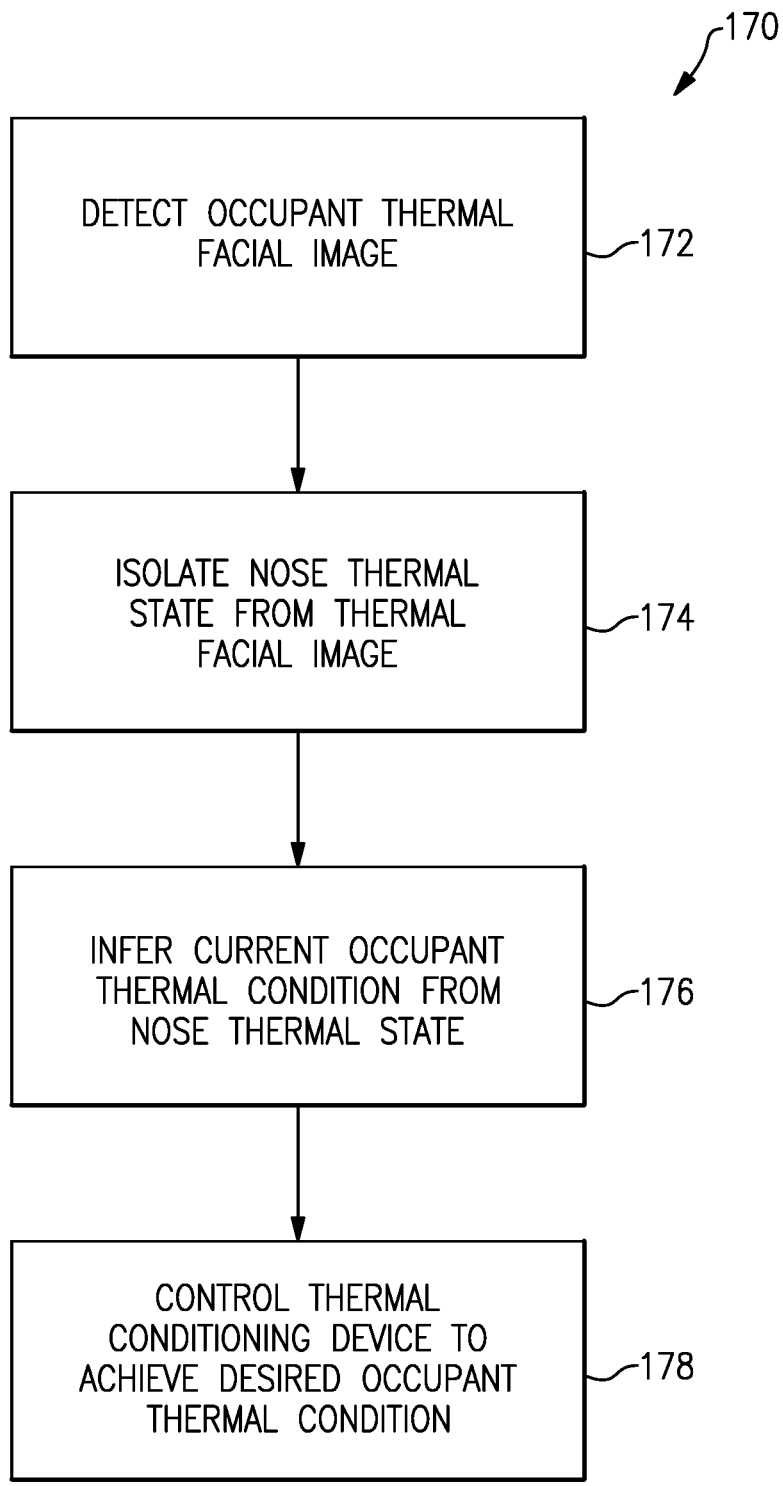
FIG. 9 is a flow chart illustrating an example method of controlling occupant thermal condition.

In operation, a method 170 of controlling a thermal state of a vehicle occupant, shown in FIG. 9, includes a step of detecting an occupant thermal facial image (block 172). In one example, the detecting step includes scanning a vehicle cabin with an infrared sensor 79 (shown in FIG. 1) to acquire a spatial array of facial temperatures from the occupant thermal facial image 152.

A nose thermal state is isolated from the occupant thermal facial image (block 174). In one example, the isolating step includes detecting a first segment corresponding to a nose of an occupant, and detecting a second segment discrete from the first segment and at least partially surrounding the nose. In one example, a nose is isolated with reference to a portion of the forehead and a portion of each cheek, which together provide the second segment, to provide the nose thermal state.

A current occupant thermal condition is inferred based upon the nose thermal state (block 176), relative to the surrounding facial temperature and by reference to, for example, a Berkeley-type reference scale, which can relatively accurately predict occupant thermal conditions if the nose is isolated from the rest of the occupant's face. The inferring step includes comparing the nose thermal state to a temperature comparison value indicative of the desired occupant thermal condition. This temperature comparison value may be a table of stored data set(s) specific to the occupant that relies upon cabin temperature, exterior vehicle temperature and occupant facial temperature, for example. In one example, the temperature comparison value may reflect a relationship that for a given occupant thermal state, the difference in temperature between the nose and surrounding area of the face increases as the cabin temperature and/or exterior vehicle temperature decreases. Generic reference data may be sufficient for accurately predicting thermal sensation from occupant-to-occupant, but more occupant-specific reference data may be need to accurately predict a given occupant's thermal comfort. Again, this occupant-specific reference data set can be "learned" over time as a given occupant interacts with the thermal conditioning system. The inferring step is performed at intervals over a period of time to determine trends, for example, useful when regulating the type and intensity of heating and cooling provided by the thermal conditioning devices.

The thermal conditioning device(s) are commanded based upon the current occupant thermal condition relative to achieve a desired occupant thermal condition (block 178). Consideration of the state of the AVA's may be used when controlling the thermal conditioning system, and the thermal conditioning device(s) may heat or cool at a variable rate based upon the thermal state of the occupant. During warm up or cool down, conventional HVAC systems operate to provide maximum heating or cooling to bring an occupant to a comfortable level in the shortest amount of time. The microclimate system according to the present disclosure, which takes into account the occupant's thermal condition, may operate the system at a reduced level of heating or cooling to bring the occupant to the desired thermal condition. In one example where an occupant who enters a cold vehicle in a warm state (i.e., slightly warm to uncomfortably warm), the microclimate system may operate the thermal conditioning devices at a reduced level to allow the cabin environment to cool the occupant for a period before bringing the cabin environment up to the desired temperature for steady state operation.

It should be noted that a controller 22 can be used to implement the various functionality disclosed in this application. The controller 22 may include one or more discrete units. Moreover, a portion of the controller 22 may be provided in the vehicle 10, while another portion of the controller 22 may be located elsewhere. In terms of hardware architecture, such a computing device can include a processor, memory, and one or more input and/or output (I/O) device interface(s) that are communicatively coupled via a local interface. The local interface can include, for example but not limited to, one or more buses and/or other wired or wireless connections. The local interface may have additional elements, which are omitted for simplicity, such as controllers, buffers (caches), drivers, repeaters, and receivers to enable communications. Further, the local interface may include address, control, and/or data connections to enable appropriate communications among the aforementioned components.

The controller 22 may be a hardware device for executing software, particularly software stored in memory. The controller 22 can be a custom made or commercially available processor, a central processing unit (CPU), an auxiliary processor among several processors associated with the controller, a semiconductor-based microprocessor (in the form of a microchip or chip set) or generally any device for executing software instructions.

The memory can include any one or combination of volatile memory elements (e.g., random access memory (RAM, such as DRAM, SRAM, SDRAM, VRAM, etc.)) and/or nonvolatile memory elements (e.g., ROM, hard drive, tape, CD-ROM, etc.). Moreover, the memory may incorporate electronic, magnetic, optical, and/or other types of storage media. The memory can also have a distributed architecture, where various components are situated remotely from one another, but can be accessed by the processor.

The software in the memory may include one or more separate programs, each of which includes an ordered listing of executable instructions for implementing logical functions. A system component embodied as software may also be construed as a source program, executable program (object code), script, or any other entity comprising a set of instructions to be performed. When constructed as a source program, the program is translated via a compiler, assembler, interpreter, or the like, which may or may not be included within the memory.

The disclosed input and output devices that may be coupled to system I/O interface(s) may include input devices, for example but not limited to, a keyboard, mouse, scanner, microphone, camera, mobile device, proximity device, etc. Further, the output devices, for example but not limited to, a printer, display, macroclimate device, microclimate device, etc. Finally, the input and output devices may further include devices that communicate both as inputs and outputs, for instance but not limited to, a modulator/demodulator (modem; for accessing another device, system, or network), a radio frequency (RF) or other transceiver, a telephonic interface, a bridge, a router, etc.

When the controller 22 is in operation, the processor can be configured to execute software stored within the memory, to communicate data to and from the memory, and to generally control operations of the computing device pursuant to the software. Software in memory, in whole or in part, is read by the processor, perhaps buffered within the processor, and then executed.

It should also be understood that although a particular component arrangement is disclosed in the illustrated embodiment, other arrangements will benefit herefrom. Although particular step sequences are shown, described, and claimed, it should be understood that steps may be performed in any order, separated or combined unless otherwise indicated and will still benefit from the present invention.

Although the different examples have specific components shown in the illustrations, embodiments of this invention are not limited to those particular combinations. It is possible to use some of the components or features from one of the examples in combination with features or components from another one of the examples.

Although an example embodiment has been disclosed, a worker of ordinary skill in this art would recognize that certain modifications would come within the scope of the claims. For that reason, the following claims should be studied to determine their true scope and content.

What is claimed is:

1. A method for controlling a thermal state of a vehicle occupant, comprising:
    obtaining an infrared (IR) image of a face of the occupant using a passive infrared sensor (PIR) sensor, the IR image comprising a spatial array of facial temperatures;
    receiving the image in a controller;
    determining a first segment of the array based on a first facial temperature associated with the first segment using the controller, the first segment corresponding to a nose of the occupant, wherein the first segment includes at least a portion of a tip of the nose;
    determining a second segment of the array at least partially surrounding the first segment based on a plurality of second facial temperatures associated with the second segment using the controller, the second segment corresponding to a region of the face surrounding the nose, wherein the second segment is in a shape of an inverted U, the second segment includes a portion of the forehead and a portion of each cheek;
    determining a difference based on the first facial temperature and at least one of the second facial temperatures using the controller; and
    determining the thermal state of the occupant based on the difference.

2. The method of claim 1, wherein the first segment has a polygonal shape with at least N sides and the second segment surrounds the first segment on at least N-1 sides, where N is an integer greater than or equal to three.

3. The method of claim 1, wherein the tip is provided by at least five pixels.

4. The method of claim 3, wherein the tip is provided by at least twelve pixels.

5. The method of claim 1, further comprising:
    obtaining a plurality of first facial temperatures within the first segment corresponding to the nose at successive T times in a period using the PIR sensor, where T is an integer greater than or equal to 2;
    obtaining a plurality of second facial temperatures corresponding to the region of the face surrounding the nose at the T times using the PIR sensor;
    determining a plurality of differences at the T times using the controller;

determining a trend in the differences;
determining a thermal comfort of the occupant based on the trend in the differences.

6. The method of claim 5, further comprising:
receiving a temperature comparison value from memory; and
determining the occupant is experiencing discomfort when the trend is increasing and the latest difference is greater than the temperature comparison value using the controller.

7. The method of claim 6, wherein the temperature comparison value corresponds to at least one of occupant thermal sensation and occupant thermal comfort.

8. The method of claim 7, wherein the at least one of occupant thermal sensation and occupant thermal comfort is based respectively on the Berkeley Sensation and Comfort Scale.

9. The method of claim 1, further comprising:
retrieving a temperature comparison value from memory of the controller, the temperature comparison value associated with one of a vasoconstricted state and a vasodilated state; and
comparing the difference and the temperature comparison value using the controller.

10. The method of claim 1, further comprising:
providing a thermal conditioning device in the vehicle that heats or cools an occupant of the vehicle at a variable heat rate; and
adjusting the variable heat rate based on the thermal state of the occupant.

11. The method of claim 10, further comprising:
commanding the thermal conditioning device based upon the difference;
wherein the adjusting step is performed in response to the commanding step.

12. The method of claim 1, wherein the first segment is spaced from the second segment.

13. The method of claim 1, wherein the nose is discrete from the second segment.

14. A thermal conditioning system comprising:
a thermal conditioning device;
an infrared sensor configured to detect an occupant thermal facial image;
a controller in communication with the thermal conditioning device and the infrared sensor, the controller configured to isolate a nose thermal state from the occupant thermal facial image and infer a current occupant thermal condition based upon the nose thermal state, wherein the occupant thermal facial image includes first and second segments, the controller configured to command the thermal conditioning device based upon the current occupant thermal condition relative to a temperature comparison value to achieve a desired occupant thermal condition, wherein the first segment includes at least a portion of a tip of the nose, wherein the nose thermal state is associated with the tip of the nose, and wherein the second segment is in a shape of an inverted U, the second segment includes a portion of the forehead and a portion of each cheek.

15. The thermal conditioning system according to claim 14, wherein the thermal conditioning device is at least one of an HVAC thermal conditioning system, a steering wheel, a seat, a door panel, an armrest, a window defogger, a dash panel and a roof panel.

16. The thermal conditioning system according to claim 14, wherein a nose is isolated with reference to a portion of the forehead and a portion of each cheek.

17. The thermal conditioning system according to claim 14, wherein the current occupant thermal condition corresponds to at least one of an occupant thermal sensation and an occupant thermal comfort.

18. The thermal conditioning system according to claim 17, wherein the at least one of occupant thermal sensation and occupant thermal comfort is based respectively on the Berkeley Sensation and Comfort Scale.

19. The thermal conditioning system according to claim 14, wherein the desired occupant thermal condition corresponds to a temperature comparison value for the nose thermal state, and the controller is configured to command the thermal conditioning device to urge the nose thermal state to the temperature comparison value.

20. A method of controlling a thermal state of a vehicle occupant, comprising:
detecting an occupant thermal facial image;
isolating a nose thermal state from the occupant thermal facial image, wherein the occupant thermal facial image includes first and second segments;
inferring a current occupant thermal condition based upon the nose thermal state, wherein the first segment includes at least a portion of a tip of the nose, wherein the nose thermal state is associated with the tip of the nose, and wherein the second segment is in a shape of an inverted U, the second segment includes a portion of the forehead and a portion of each cheek; and
commanding a thermal conditioning device based upon the current occupant thermal condition relative to achieve a desired occupant thermal condition.

21. The method according to claim 20, wherein the detecting step includes scanning a vehicle cabin with an infrared sensor to acquire a spatial array of facial temperatures from the occupant thermal facial image.

22. The method according to claim 20, wherein the isolating step includes detecting the first segment corresponding to a nose of an occupant, detecting the second segment discrete from the first segment and at least partially surrounding the nose.

23. The method according to claim 20, wherein the inferring step includes comparing the nose thermal state to a temperature comparison value indicative of the desired occupant thermal condition.

24. The method according to claim 23, wherein the temperature comparison value is a stored data set specific to an occupant.

25. The method according to claim 20, wherein the inferring step is performed at intervals over a period of time.

26. The method according to claim 20, wherein the thermal conditioning device is at least one of an HVAC thermal conditioning system, a steering wheel, a seat, a door panel, an armrest, a window defogger, a dash panel and a roof panel.

* * * * *